US010485862B2

(12) United States Patent
Dhere et al.

(10) Patent No.: US 10,485,862 B2
(45) Date of Patent: Nov. 26, 2019

(54) METHODS FOR ENTEROVIRUS INACTIVATION, ADJUVANT ADSORPTION AND DOSE REDUCED VACCINE COMPOSITIONS OBTAINED THEREOF

(71) Applicant: SERUM INSTITUTE OF INDIA PRIVATE LIMITED, Maharashtra, Pune (IN)

(72) Inventors: Rajeev Mhalasakant Dhere, Pune (IN); Sambhaji Shankar Pisal, Pune (IN); Jagdish Kamalaji Zade, Pune (IN); Rajendra Narayan Sabale, Pune (IN)

(73) Assignee: SERUM INSTITUTE OF INDIA PVT LTD, Maharashtra Pune (IN)

( * ) Notice: Subject to any disclaimer, the term of this patent is extended or adjusted under 35 U.S.C. 154(b) by 53 days.

(21) Appl. No.: 15/517,225

(22) PCT Filed: Oct. 6, 2015

(86) PCT No.: PCT/IN2015/000376
§ 371 (c)(1),
(2) Date: Apr. 6, 2017

(87) PCT Pub. No.: WO2016/063291
PCT Pub. Date: Apr. 28, 2016

(65) Prior Publication Data

US 2017/0348411 A1 Dec. 7, 2017

(30) Foreign Application Priority Data

Oct. 7, 2014 (IN) ......................... 3180/MUM/2014

(51) Int. Cl.

| | |
|---|---|
| ***A61K 39/13*** | (2006.01) |
| ***A61K 39/39*** | (2006.01) |
| ***C12N 7/06*** | (2006.01) |
| ***C12N 7/04*** | (2006.01) |
| ***C12N 7/00*** | (2006.01) |
| *A61K 39/00* | (2006.01) |

(52) U.S. Cl.
CPC .............. *A61K 39/13* (2013.01); *A61K 39/39* (2013.01); *C12N 7/00* (2013.01); *C12N 7/045* (2013.01); *C12N 7/06* (2013.01); *A61K 2039/5252* (2013.01); *A61K 2039/5254* (2013.01); *A61K 2039/545* (2013.01); *A61K 2039/55505* (2013.01); *A61K 2039/575* (2013.01); *A61K 2039/70* (2013.01); *C12N 2770/32334* (2013.01); *C12N 2770/32634* (2013.01); *C12N 2770/32663* (2013.01); *C12N 2770/32671* (2013.01); *Y02A 50/383* (2018.01); *Y02A 50/386* (2018.01); *Y02A 50/388* (2018.01); *Y02A 50/39* (2018.01); *Y02A 50/392* (2018.01); *Y02A 50/412* (2018.01); *Y02A 50/466* (2018.01); *Y02A 50/484* (2018.01)

(58) Field of Classification Search
None
See application file for complete search history.

(56) References Cited

FOREIGN PATENT DOCUMENTS

WO 2008028956 A1 3/2008

OTHER PUBLICATIONS

Barteling et al. Formaldehyde Inaetivation of Foot-and-Mouth Disease Virus. Conditions for the Preparation of Safe Vaccine. Archives of Virology 80, 103--t17 (1984).*

Tano et al. Antigenic characterization of a formalin-inactivated poliovirus vaccine derived from live-attenuated Sabin strains. Vaccine 25 (2007) 7041-7046.*

Hawken et al. Adjuvants and inactivated polio vaccine: A systematic review. Vaccine 30 (2012) 6971-6979.*

Medium 199 . Sigma-Aldrich. https://www.sigmaaldrich.com/life-science/cell-culture/classical-media-salts/medium-199.html.*

World Health Organization. Combined Immunization of Infants with Oral and Inactivated Poliovirus Vaccines: Results of a Randomized Trial in The Gambia, Oman, and Thailand. The Journal oflnfectious Diseases 1997;175(SuppII):S215-27.*

Floyd et al. Viral Aggregation: Buffer Effects in the Aggregation of Poliovirus and Reovirus at Low and High pH. Applied and Environmental Microbiology, Sep. 1979, vol. 38, No. 3, p. 395-401.*

* cited by examiner

*Primary Examiner* — Nianxiang Zou
(74) *Attorney, Agent, or Firm* — Baker & Hostetler LLP

(57) ABSTRACT

The present invention is directed to improved methods of Enterovirus inactivation by formaldehyde in presence of tromethamine buffer resulting in maximum recovery of D-antigen. Subsequent adsorption of said sIPV on aluminium hydroxide provides significantly dose reduced sIPV compositions.

21 Claims, 4 Drawing Sheets

METHODS FOR ENTEROVIRUS INACTIVATION, ADJUVANT ADSORPTION AND DOSE REDUCED VACCINE COMPOSITIONS OBTAINED THEREOF

CROSS REFERENCE TO RELATED APPLICATIONS

This application is a National Stage of International Application No. PCT/IN2015/000376, filed on Oct. 6, 2015, which claims priority to Indian patent application no. 3180/MUM/2014, filed on Oct. 7, 2014, the disclosures of which are incorporated by reference in their entirety.

BACKGROUND OF THE INVENTION

The prevalence of polio virus has largely been decreased by the use of Oral Polio Vaccine (OPV), based on live-attenuated Sabin polio strains. However, OPV has limitations for the post-eradication era. Therefore, development of Sabin-IPV plays an important role in the WHO polio eradication strategy. The use of attenuated Sabin instead of wild-type Salk polio strains will provide additional safety during vaccine production. Moreover, to prevent the emergence of circulating vaccine-derived polioviruses (cVDPVs), the use of OPV should be discontinued following polio eradication, and replaced by IPV. These cVDPVs are transmissible and can become neurovirulent (similar to wild polioviruses) resulting in vaccine associated paralytic poliomyelitis. Such strains can potentially re-seed the world with polioviruses and negate the eradication accomplishments.

IPV is delivered by intramuscular (IM) or deep subcutaneous (SC) injection. IPV is currently available either as a non-adjuvanted stand-alone formulation, or in various combinations, including DT-IPV (with diphtheria and tetanus toxoids) and hexavalentDTPHepB-Hib-IPV vaccines (additionally with pertussis, hepatitis B, and *Haemophilus influenzae* b. The currently acceptable standard dose of polio vaccines contains D antigens as 40 Units of inactivated poliovirus type 1 (Mahoney), 8 units of inactivated poliovirus type 2 (MEF-I) and 32 units of inactivated poliovirus type 3 (Saukett) (e.g. Infanrix-IPV™). Existing preparations of stand-alone IPV do not contain adjuvant.

Most experts agree that worldwide use of IPV is preferable because of its proven protective track-record and safety. However, when compared to OPV, the cost-prize for IPV is significantly higher. This is mainly due to requirements for: (i) more virus per dose; (ii) additional downstream processing (i.e. concentration, purification and inactivation), and the related QC-testing (iii) loss of antigen or poor recovery in downstream and iv) containment. Until now, the financial challenge has been a major drawback for IPV innovation and implementation in low and middle-income countries. The production costs of sIPV are currently estimated equivalent to that for IPV, which is about 20-fold more expensive than OPV. The future global demand for IPV following eradication of polioviruses could increase from the current level of 80 million doses to 450 million doses per year. Consequently, approaches to “stretch” supplies of IPV are likely to be required.

Reduced-dose efficacious vaccine formulations which provide protection against infection using a lower dose of IPV antigen are desirable in situations where the supply of conventional vaccine is insufficient to meet global needs or where the cost of manufacture of the conventional vaccine prevents the vaccine being sold at a price which is affordable for developing countries. Also the exposure to lower dose of IPV; compared to the existing marketed formulations could be more safer. Thus, various strategies to make IPV available at more affordable prices need to be evaluated.

In case of pandemic influenza vaccines the use of adjuvants has permitted dose reduction, increased the availability and reduced cost of the vaccine. Therefore, it has been speculated that an adjuvanted vaccine formulation of sIPV would reduce cost and also increase the number of available sIPV doses worldwide.

Globally different research groups have been evaluating dose sparing for vaccines (Influenza vaccines in particular) by employing several adjuvants namely Alum, Emulsion, TLR-agonists (MPL, CpG, poly-IC, imiquimod), dmLT, 1,25-dihydroxyvitamin D3, CAF01, poly [di (carboxylatophenoxy)-phosphazene] (PCPP) and Venezuelan equine encephalitis (VEE) replicon particles. Most of the adjuvant types being studied have encountered following hurdles i) Unknown safety or classified as toxic by regulatory agencies ii) having limitations regards to route of administration iii) lacking manufacturing reproducibility iv) stability of adjuvant.

Emulsion adjuvants (MF-59, AS03, AF3) have been previously reported to provide a strong dose-reduction effect (>30 fold) for Influenza and Hepatitis B vaccines. These adjuvants work by forming a depot at the site of injection, enabling the meted release of antigenic material and the stimulation of antibody producing plasma cells. However, these adjuvants have been deemed too toxic for widespread human prophylactic vaccine use and are usually reserved for those severe and/or terminal conditions such as cancer where there is a higher tolerance of side-effects.

Further, Aluminum salts have been considered safe, are already being used in combination vaccines containing sIPV, have the lowest development hurdles and are inexpensive to manufacture. However aluminium adjuvants are not known for permitting significant dose-reduction.

One of the most critical steps in the production of vaccines against pathogens, in particular viral vaccines, is viral inactivation. In the case of virus inactivation, formalin is the most frequently used inactivating agent in the manufacture of vaccines. Formaldehyde inactivates a virus by irreversibly cross-linking primary amine groups in surface proteins with other nearby nitrogen atoms in protein or DNA through a —CH2-linkage. A potential problem with using formalin for viral inactivation is that this involves a series of chemical reactions that produce reactive products that can induce cross-linking of viral proteins and aggregation of virus particles. This could hamper the inactivating efficiency of the formalin and could also result in the partial destruction of the immunogenicity of the antigen in vaccine. Accordingly, it has been reported previously that formalin inactivation of polioviruses could affect the viral immunogenicity as well as antigenicity. Refer Morag Ferguson et al Journal of General Virology (1993), 74, 685-690. Most importantly, previously disclosed formaldehyde inactivation methods were particularly carried out in presence of phosphate buffer wherein significant D-antigen losses were observed along with epitope modification for Sabin Type I/II/III (D-antigen recovery post inactivation: 22% for sabin type I, 15% for sabin type II, 25% for sabin type III), thereby failing to preserve the epitopic conformation. It is therefore possible that antibodies produced by recipients of formalin-inactivated polioviruses (in presence of phosphate buffer) may not contribute to the protective immune response.

By combining formalin and UV-inactivation, scientists tried to overcome the limitations of isolated UV-inactivation or formalin-inactivation, respectively, when inactivating the particularly resilient poliovirus. See, e.g., McLean, et al., "Experiences in the Production of Poliovirus Vaccines," Prog. Med. Virol., vol 1, pp. 122-164 (1958.) Taylor et al. (J. Immunol. (1957) 79:265-75) describe the inactivation of poliomyelitis virus with a formalin and ultraviolet combination. Molner et al. (Am. J. Pub. Health (1958) 48:590-8) describe the formation of a measurable level of circulating antibodies in the blood of subjects vaccinated with ultraviolet-formalin inactivated poliomyelitis vaccine. Truffelli et al. (Appl. Microbiol. (1967) 15:516-27) report on the inactivation of Adenovirus and Simian Virus 40 Tumorigenicty in hamsters by a three stage inactivation process consisting of formalin, UV light and β-propiolactone (BPL). Miyamae (Microbiol. Immunol. (1986) 30:213-23) describes the preparation of immunogens of Sendai virus by a treatment with UV rays and formalin. However previously discussed promising alternatives for formaldehyde like β-propiolactone (BPL) have been reported to produce an immune complex-reaction when combined with other components of the rabies vaccine. Additionally, it has been shown to produce squamous cell carcinomas, lymphomas and hepatomas in mice.

It is therefore particularly desirable to employ favorable formaldehyde inactivation conditions that maintain the structural integrity of antigenic structures of Sabin strains as well as utilize safe and cost-effective adjuvants that can result in significantly dose reduced (i.e. 8 to 10 fold) sIPV (Sabin IPV) vaccine compositions thereby reducing cost of manufacture, increasing vaccine supplies and making vaccines affordable for developing countries.

The present inventors have surprisingly found that D-antigen losses post-formaldehyde inactivation could be due to presence of phosphate buffer that unexpectedly causes undesirable aggregation of polio viruses. The instant invention provides an improved process of formaldehyde inactivation in presence of TRIS buffer thereby ensuring minimal epitopic modifications and subsequently minimizing D-antigen losses. Subsequently significantly dose reduced Sabin IPV vaccine compositions with atleast 8 fold dose reduction for Sabin Type I and 3 fold dose reduction for Sabin Type III can be obtained.

DETAILED DESCRIPTION

Figure 1:
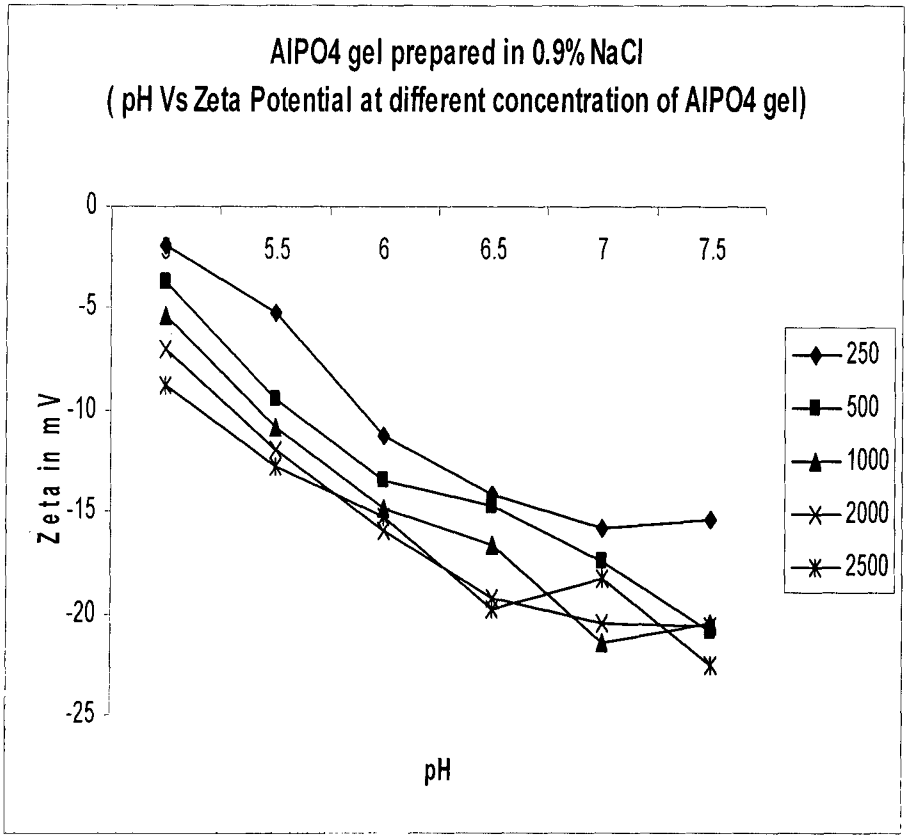
FIG. 1: Alum phosphate gel prepared in 0.9% NaCl (pH Vs Zeta potential at different concentrations of Alum phosphate gel)

An important aspect of the instant invention is that said improved process of formalin inactivation and adsorption on alum salt comprises of following steps:

a) Adding Sabin IPV purified bulk to TRIS buffer (30 to 50 mM) having pH between 6.8 to 7.2,
b) Adding M-199 medium containing glycine (5 gm/l) to mixture of (a),
c) Adding 0.025% formaldehyde while mixing,
d) Incubating mixture obtained in Step (c) at 37° C. from 5 to 13 days on magnetic stirrer,
e) Subjecting post-incubation mixture to intermediate 0.22μ filtration on day 7 and final filtration on day 13,
f) Storing bulk obtained after step (e) at 2-8° C.,
g) Performing D-Ag ELISA for D-Antigen unit determination,
h) Taking the desired volume of autoclaved $Al(OH)_3$ to get the final concentration of Alum(Al++) between 0.8 to 1.2 mg/dose in a 50 ml Container,
i) Adding sIPV bulk with adjusted D-Ag unit and making up the volume with diluent (10×M-199+0.5 Glycine %),
j) Adjusting the final formulation pH and obtaining final formulation with pH between 6 and 6.5,
k) Subjecting the formulation bulk to magnetic stirring overnight at 2-8° C. and wherein formalin inactivation of step (a) does not occur in presence of phosphate buffer A first embodiment of instant invention is that said buffer to be used during formaldehyde inactivation can be selected from the group consisting of TRIS, TBS, MOPS, HEPES, and bicarbonate buffers.

A preferred aspect of first embodiment is that said formaldehyde inactivation can occur in presence of TRIS Buffer or TBS (TRIS Buffered saline) having concentration selected from 30 mM, 40 mM and 50 mM, preferably 40 mM and at a pH selected from 6.8, 6.9, 7, 7.1 and 7.2, preferably between 6.8 and 7.2 wherein said inactivation does not utilize any phosphate buffer.

A second embodiment of the instant invention is that adsorption of formalin inactivated sIPV can be done on aluminium hydroxide having concentration selected from 1.5 mg/dose, 1.8 mg/dose, 2.2 mg/dose, preferably between 2 mg/dose to 2.4 mg/dose and at a pH selected from 6.2, 6.3, 6.4 and 6.5, preferably 6.5.

A third embodiment of instant invention is that said improved process of formalin inactivation and aluminium hydroxide adsorption can result in D-Antigen recovery post-inactivation between 50% and 80% and percent adsorption of aluminium hydroxide can be between 85 and 99%.

One aspect of third embodiment is that present invention provides an improved process of formalin inactivation and aluminium hydroxide adsorption resulting in dose reduction of atleast 8 fold for Sabin Type I, atleast 3 fold for Sabin Type III as compared to standard dose of 40 DU-8DU-32DU. Second aspect of third embodiment is that instant invention provides improved formaldehyde inactivation and aluminium hydroxide adsorption methods that result in vaccine compositions comprising of i) inactivated poliovirus type 1 at a dose of atleast 5D-antigen units, ii) inactivated poliovirus type 2 at a dose of atleast 8D-antigen units and iii) inactivated poliovirus type 3 at a dose of atleast 10D-antigen units.

A fourth embodiment of instant invention is that said aluminium salt adjuvant is an aluminium hydroxide having concentration between 1.5 mg/0.5 ml dose and 2.5 mg/0.5 ml dose, preferably between 2.100 mg/0.5 ml dose and 2.4 mg/0.5 ml dose at a pH of about 6.5.

One aspect of fourth embodiment is that total aluminium content in the trivalent vaccine (Type 1, 2 and 3) can be between 800-1000 μg, preferably 800 μg $Al^{3+}$+ per 0.5 mL dose, characterized in that atleast 400 μg $Al^{3+}$ for Type 1, atleast 200 μg $Al^{3+}$ for Type 2, atleast 200 μg $Al^{3+}$ for Type 3.

Another aspect of fourth embodiment is that said dose reduced polio virus vaccine composition can consist of Type 1 and Type 3 and is devoid of Type 2 wherein the dose volume can be between 0.1 and 0.4 ml.

The dose reduced vaccine compositions prepared by instant methods can be i) "Standalone sIPV" wherein the antigens may comprise of sIPV type 1 or sIPV type 2 or sIPV type 3, or sIPV types 1 and 2, or sIPV types 1 and 3, or sIPV types 2 and 3, or sIPV types 1, 2 and 3 or ii) "Combination Vaccines containing sIPV" wherein said non-IPV antigens of combination vaccines can be selected from but not limited to diphtheria toxoid, tetanus toxoid, whole cell pertussis antigen(s), acellular pertussis antigen(s), Hepatitis B surface antigen, *Haemophilus influenzae* b antigen(s), *Neisseria meningitidis* A antigen(s), *Neisseria meningitidis* C antigen(s), *Neisseria meningitidis* W-135 antigen(s), *Neisseria meningitidis* Y antigen(s), *Neisseria meningitidis* X antigen(s), *Neisseria meningitidis* B bleb or purified antigen(s), Hepatitis A antigen(s), *Salmonella typhi* antigen(s), *Streptococcus pneumoniae* antigen(s).

The non-IPV antigen(s) may be adsorbed onto an aluminium salt such as aluminium hydroxide, an aluminium salt such as aluminium phosphate or onto a mixture of both aluminium hydroxide and aluminium phosphate, or may be unadsorbed.

Poliovirus may be grown in cell culture. The cell culture may be a VERO cell line or PMKC, which is a continuous cell line derived from monkey kidney. VERO cells can conveniently be cultured microcarriers. After growth, virions may be purified using techniques such as ultrafiltration, diafiltration, and chromatography. Prior to administration to patients, the viruses must be inactivated, and this can be achieved by treatment with formaldehyde.

Compositions may be presented in vials, or they may be presented in ready filled syringes. The syringes may be supplied with or without needles. A syringe will include a single dose of the composition, whereas a vial may include a single dose or multiple doses (e.g. 2 doses). In one embodiment the dose is for human. In a further embodiment the dose is for an adult, adolescent, toddler, infant or less than one year old human and may be administered by injection.

Vaccines of the invention may be packaged in unit dose form or in multiple dose form (e.g. 2 doses). The said multidose composition can be selected from a group consisting of 2 dose, 5 dose and 10 dose. For multiple dose forms, vials are preferred to pre-filled syringes. Effective dosage volumes can be routinely established, but a typical human dose of the composition for injection has a volume of 0.5 mL.

EXAMPLES

Example 1

Purification of Sabin IPV (sIPV)

1) Tangential Flow Filtration (TFF):

Clarified harvest pool was concentrated to 10× using tangential flow filtration system with 100 Kda cassettes ($0.5\ m^2$) and then diafiltered 3 times of harvest volume with phosphate buffer (40 mM, pH: 7.0)

2) Column Chromatography:

The purification was done by Ion Exchange Chromatography (IEC). 10×TFF concentrate was passed through DEAE Sepharose fast flow (Weak-Anion exchanger) packed in column xk-26 using Akta explorer (GE Healthcare). Negatively charged impurities was found to bind to the column whereas polio virus was collected in flow through with phosphate buffer 40 mM.

3) TRIS Buffer Exchange:

To minimize the loss of antigen in a quite cumbersome inactivation procedure (13 days), purified virus pool was buffer exchanged from phosphate buffer to TRIS buffer (40 mM, pH: 7) with TFF system (100 KDa, 0.1 m2). The purified virus pool was exchanged with three volumes of tris buffer.

Example 2

A) Inactivation of sIPV

10× concentrated M-199 with 0.5% glycine was added so as to achieve final concentration 1×. Inactivation agent formalin (0.025%) was added into purified virus bulk while constant mixing. Inactivation was carried out at 37° C. while continuous stirring for 13 days containing 0.22 u filtration on 7th day and 13th day.

B) Inactivation of sIPV in TRIS Buffer and Phosphate Buffer 0.025% formaldehyde was used for inactivation for 13 days at 37° C.

TABLE 1

D-Antigen Content, Formalin inactivation in presence of TRIS buffer and Phosphate buffer

| | D-Antigen content (40 mM Phosphate buffer during Inactivation) | D-Antigen content (40 mM Tris buffer during Inactivation) |
|---|---|---|
| Type 1 | 52.70 DU/ml | 408.19 DU/ml |
| Type 2 | 22.63 | 180.20 |
| Type 3 | 4.21 | 21.50 |

When formaldehyde inactivation methods were particularly carried out in presence of phosphate buffer, significant D-antigen losses were observed for Sabin Type I. Whereas it was found that formaldehyde inactivation in presence of TRIS buffer resulted in minimum loss of D-antigen.

TABLE 2

Different concentrations of TRIS Buffer used during inactivation

| | 30 mM | 40 mM | 50 mM |
|---|---|---|---|
| Type 1 | 500 DU/ml | 576.80 DU/ml | 585 DU/ml |
| Type 2 | 140 DU/ml | 165.16 DU/ml | 155 DU/ml |
| Type 3 | 16 DU/ml | 21.17 DU/ml | 19 DU/ml |

TRIS Buffer at a concentration of 40 mM was found to be most efficient in terms of D-Antigen content preservation for sIPV 1, 2 and 3.

C) D-Antigen Content Determination by ELISA.

Day 1: Plate Coating:

1. 100 ul of specific bovine anti polio was pipetted in PBS per well
2. Microtiter plate was sealed and incubated overnight at room temperature.

Day 2: Blocking:

1. The plates were washed (Washing/dilution buffer –0.05% tween 20 in 1×PBS) 3 times.
2. 300 ul block buffer (1% BSA in PBS) was pipetted per well.
3. The plate was sealed and incubated for 45 minutes at 37±1° C.

Sample Addition:

1. The plate was washed 3 times.
2. 100 ul of sample diluent was added in all wells except well of row A.
3. 100 ul standard was added to first two wells of column 2 and 3.
4. 100 ul sample was added to first two wells of column 4-12.
5. Prediluting sample to a suitable concentration.
6. 100 ul sample diluents was added to first two wells of column 1.
7. Serial two fold dilution were made down the column by transferring 100 ul from each well to adjacent well of the same column and discarding 100 ul from the last well.
8. Incubating at 37° C. for 2 hr.
9. Plates were kept overnight at 4° C.

Day 3: Monoclonal Antibody Addition:

1. The plate was washed 3 times.
2. 100 ul diluted (1:240) type specific monoclonal antibodies were added.
3. The plates were sealed and incubated for 2 hours at 37° C.

Conjugate:

1. The plate were washed 3 times
2. 100 ul diluted conjugate (Type1-1:2400, Type2-1:1500, Type3-1:4800) was added.
3. The plate was sealed and incubated for 1 hour at 37° C.

Substrate Addition:

1. 100 ul TMB substrate was added to all wells.
2. Mixture incubated at room temperature for 10 minutes.
3. Reaction was stopped by adding 100 ul 2M H2SO4.
4. Plate was read at 450/630 nm.
5. D antigen concentration was calculated using KC4 software.

Example 3

Adsorption of sIPV:

1. Autoclaved 1% stock of $Al(OH)_3$ and $AlPO_4$ was used for the preparation of formulations.
2. Desired volume of $Al(OH)_3/AlPO_4$ was taken to get the required concentration of alum in a 100 ml glass bottle.
3. Inactivated polio virus bulk with known D-Ag Unit was added and volume make up was done with diluent.
4. Final formulation pH was adjusted to 6.5 with 1 N HCl/NaOH.
5. The formulation bulk was kept on magnetic stirrer overnight at 2-8° C.

Example 4

Preformulation Studies

Different concentrations of $Al(OH)_3$ & $AlPO_4$ were prepared in 0.9% saline and in WFI to check size and zeta potential with respect to change in pH.

Figure 2:
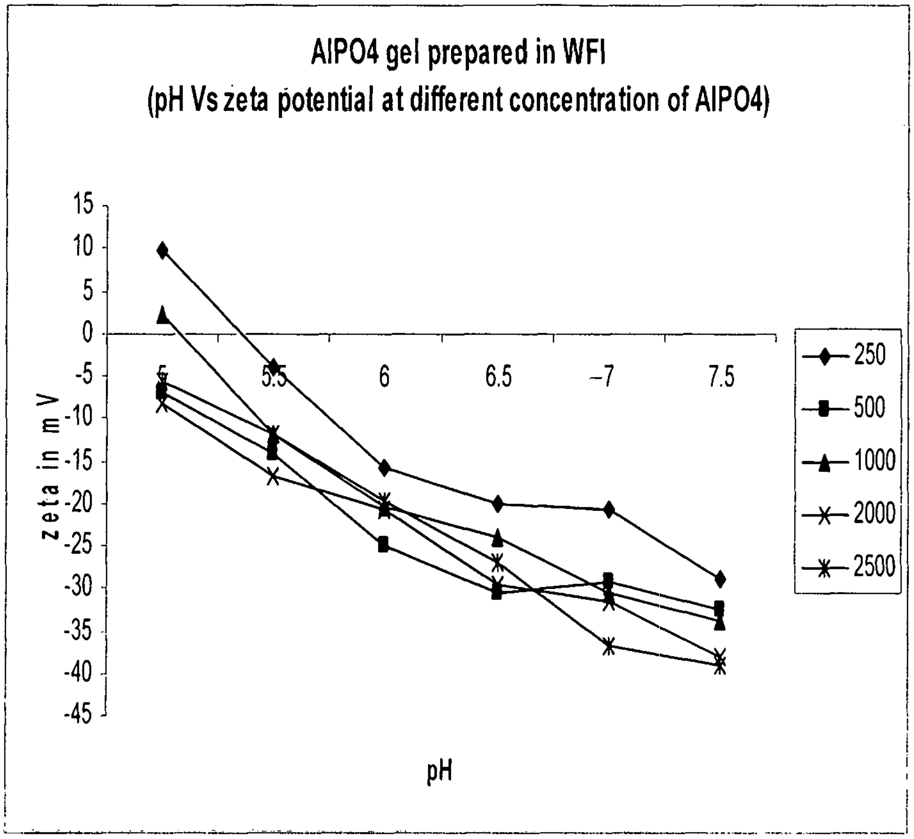
FIG. 2: Alum phosphate gel prepared in WFI (pH Vs Zeta potential at different concentrations of Alum phosphate gel)

It was observed that zeta potential of $AlPO_4$ decreases (negativity) with increase in pH from 5 to 7.5 in presence of WFI as well as in saline (Refer FIGS. 1 and 2).

Figure 3:
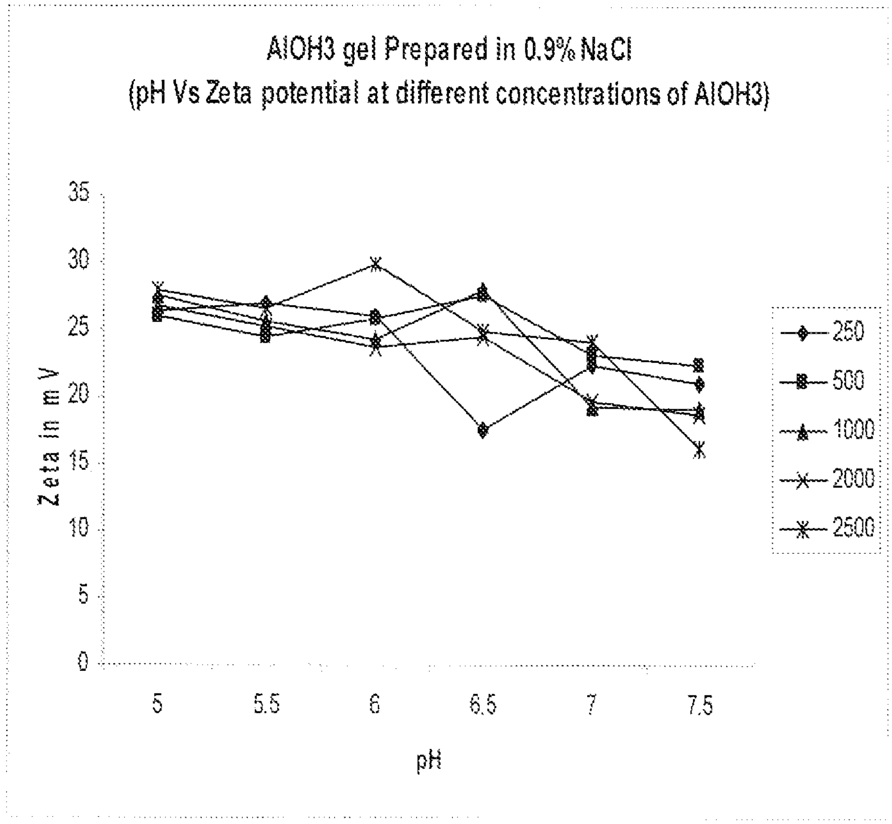
FIG. 3: Alum Hydroxide gel prepared in 0.9% NaCl (pH Vs Zeta potential at different concentrations of Alum hydroxide gel)
Figure 4:
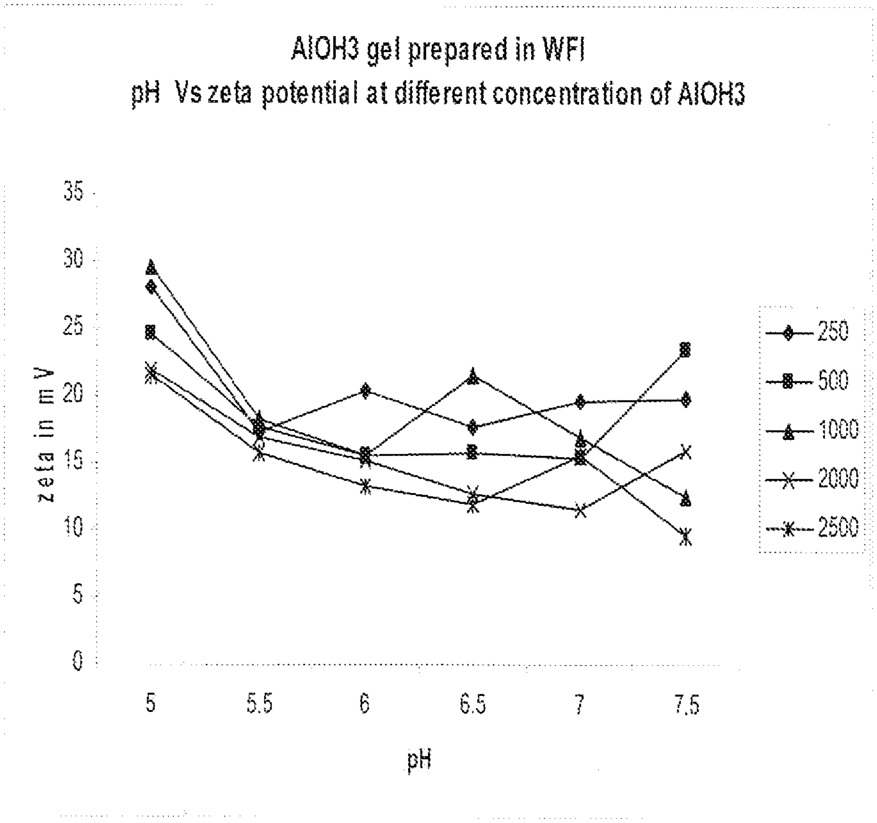
FIG. 4: Alum Hydroxide gel prepared in WFI (pH Vs Zeta potential at different concentrations of Alum hydroxide gel)

Whereas, zeta potential of $Al(OH)_3$ in saline remains constant, independent of pH and $Al(OH)_3$ salt concentration (Refer FIGS. 3 and 4).

Example 5

Adsorption Studies of sIPV on Alum Phosphate and Alum Hydroxide

TABLE 3

Sabin Type 1, 2&3 (Titer $10^{6.0}$/dose) adsorption on alum (Alum phosphate and Alum Hydroxide)

| | Sample | Titer (per does) | Virus Particles (in K) | % free in SUP | % adsorbed on gel |
|---|---|---|---|---|---|
| Type 1, $AlOH_3$ | Control | 5.45 | 284 | NA | |
| | Al+++ 125 ug/dose | 4.15 | 14 | 4.98 | 95.02 |
| | Al+++ 250 ug/dose | 3.85 | 7 | 2.49 | 97.51 |
| | Al+++ 500 ug/dose | 3.8 | 6.3 | 2.24 | 97.78 |
| Type 1, $AlPO_4$ | Control | 5.84 | 691 | NA | |
| | Al+++ 125 ug/dose | 3.49 | 3 | 0.43 | 99.57 |
| | Al+++ 250 ug/dose | 3.09 | 1.2 | 0.17 | 99.83 |
| | Al+++ 500 ug/dose | 2.94 | 0.87 | 0.12 | 99.87 |
| Type 2, $AlOH_3$ | Control | 5.49 | 309 | NA | |
| | Al+++ 125 ug/dose | 3.59 | 3.89 | 1.25 | 98.75 |
| | Al+++ 250 ug/dose | 3.49 | 3.09 | 1 | 99 |
| | Al+++ 500 ug/dose | 3.49 | 3.09 | 1 | 99 |
| Type 2, $AlPO_4$ | Control | 5.49 | 309 | NA | |
| | Al+++ 125 ug/dose | 3.15 | 1.41 | 0.45 | 99.5 |
| | Al+++ 250 ug/dose | 3.09 | 1.23 | 0.39 | 99.6 |
| | Al+++ 500 ug/dose | 3.09 | 1.23 | 0.39 | 99.6 |
| Type 3, $AlOH_3$ | Control | 5.59 | 389 | NA | |
| | Al+++ 125 ug/dose | 4.14 | 13.8 | 3.54 | 96.47 |
| | Al+++ 250 ug/dose | 3.94 | 8.7 | 2.23 | 97.77 |
| | Al+++ 500 ug/dose | 3.54 | 3.4 | 0.87 | 99.13 |
| Type 3, $AlPO_4$ | Control | 5.59 | 389 | NA | |
| | Al+++ 125 ug/dose | 5.34 | 218 | 56.04 | 43.96 |
| | Al+++ 250 ug/dose | 5.24 | 173 | 44.47 | 55.53 |
| | Al+++ 500 ug/dose | 5.16 | 144 | 37.01 | 62.9 |

It was found that Sabin polio virus type-3 shows only 50-60% adsorption with aluminium phosphate ($AlPO_4$). Whereas, Sabin polio virus type-3 shows atleast 90% adsorption with $Al(OH)_3$. Thus, Alum hydroxide was found to be more efficient as compared to Alum phosphate with respect to adsorption of Sabin Type 1, 2 and 3.

Example 6

Immunogenicity Studies of Alum Adsorbed sIPV

To check immune response of adjuvanted sIPV in rat (Sera Neutralisation Test) SNT test was carried out. Sera was separated and used to test the presence of neutralizing antibodies for type specific polio virus. Control sera used to validate the test. Virus back-titration was also performed to get the number of challenge virus particles added.

Animal Model: Wistar rat (8 weeks, approx 200 gm) 50% male and 50% female per group.

Route of Inoculation: Intra Muscular.

Volume: 0.5 ml

Blood withdrawal: on day 21.

Site of bleeding: Retro-Orbital plexus.

TABLE 6

| Type 3 | | | | | | |
|---|---|---|---|---|---|---|
| | Group 1 | | Group 2 | | Group 3 | |
| | Al(OH)3 Adjuvanted | | | | | |
| | 10 DU 0.6 mgOH | | 5 DU 0.6 mgOH | | 2.5 DU 0.6 mgOH | |
| Rat No | SNT +ve | Sera Titer | SNT +ve | Sera Titer | SNT +ve | Sera Titer |
| 1 | 3 | (1:8) | 2 | (1:4) | 0 | (<1:2) |
| 2 | 0 | (<1:2) | 5 | (1:32) | 1 | (1:2) |
| 3 | 2 | (1:4) | 3 | (1:8) | 1 | (1:2) |
| 4 | 4 | (1:16) | 2 | (1:4) | 0 | (<1:2) |
| 5 | 4 | (1:16) | 2 | (1:4) | 1 | (1:2) |

TABLE 4

| Type 1 | | | | | | | | | | | | | | | | |
|---|---|---|---|---|---|---|---|---|---|---|---|---|---|---|---|---|
| | Group 1 Comm. IPV | | Group 2 5 DU 1.15 mgOH | | Group 3 2.5 DU 1.15 mgOH | | Group 4 1 DU 1.15 mgOH | | Group 5 5 DU 1.8 mgPO4 | | Group 6 2.5 DU 1.8 mgPO4 | | Group 7 1 DU 1.8 mgPO | | Group 15 −ve control | |
| Rat No | SNT +ve | Sera Titer | SNT | Sera Titer | SNT | Sera Titer | SNT | Sera Titer | SNT | Sera Titer | SNT +ve | Sera Titer | SNT | Sera Titer | SNT | Sera Titer |
| 1 | 1 | (1:2) | 8 | (1:256) | 1 | (1:2) | 4 | (1:16) | 5 | (1:32) | 5 | (1:32) | 2 | (1:4) | 0 | (<1:2) |
| 2 | 1 | (1:2) | 5 | (1:32) | 1 | (1:2) | 7 | (1:128) | 8 | (1:256) | 4 | (1:16) | 1 | (1:2) | 0 | (<1:2) |
| 3 | 0 | (<1:2) | 7 | (1:128) | 3 | (1:8) | 0 | (<1:2) | 4 | (1:16) | 6 | (1:64) | 0 | (<1:2) | 0 | (<1:2) |
| 4 | 0 | (<1:2) | 11 | (1:2048) | 2 | (1:4) | 2 | (1:4) | 1 | (1:2) | 5 | (1:32) | 0 | (<1:2) | 0 | (<1:2) |
| 5 | 7 | (1:128) | 3 | (1:8) | 7 | (1:128) | 5 | (1:32) | 6 | (1:64) | 4 | (1:16) | 1 | (1:2) | 0 | (<1:2) |
| 6 | 4 | (1:16) | 7 | (1:128) | 7 | (1:128) | 1 | (1:2) | 5 | (1:32) | 6 | (1:64) | 3 | (1:8) | 0 | (<1:2) |
| 7 | 3 | (1:8) | 5 | (1:32) | 4 | (1:16) | 1 | (1:2) | 8 | (1:256) | 7 | (1:128) | 0 | (<1:2) | 0 | (<1:2) |
| 8 | 1 | (1:2) | 7 | (1:128) | 3 | (1:8) | 2 | (1:4) | 6 | (1:64) | 0 | (<1:2) | 0 | (<1:2) | 0 | (<1:2) |
| 9 | 3 | (1:8) | 8 | (1:256) | 2 | (1:4) | 3 | (1:8) | 8 | (1:256) | 4 | (1:16) | 4 | (1:16) | 0 | (<1:2) |
| 10 | 3 | (1:8) | 7 | (1:128) | 4 | (1:16) | 5 | (1:32) | 6 | (1:64) | 2 | (1:4) | 2 | (1:4) | 0 | (<1:2) |

It was surprisingly found that Alum hydroxide adjuvanted Type 1 Sabin IPV having 5 DU/dose gave better seroconversion as compared to Salk IPV vaccine with 40 DU/dose and Alum phosphate adjuvanted Sabin IPV having 5 DU/dose.

TABLE 5

| Type 2 | | | | | | |
|---|---|---|---|---|---|---|
| | Group 1 | | Group 2 | | Group 3 | |
| | Al(OH)3 Adjuvanted | | | | | |
| | 4 DU(0.6 mgOH) | | 8 DU(0.6 mgOH) | | 16 DU 0.6 mgOH | |
| Rat No | SNT +ve | Sera Titer | SNT +ve | Sera Titer | SNT +ve | Sera Titer |
| 1 | 3 | (1:8) | 4 | (1:16) | 7 | (1:128) |
| 2 | 4 | (1:16) | 6 | (1:64) | 5 | (1:32) |
| 3 | 0 | (<1:2) | 3 | (1:8) | 5 | (1:32) |
| 4 | 3 | (1:8) | 4 | (1:16) | 6 | (1:64) |
| 5 | 5 | (1:32) | 7 | (1:128) | 6 | (1:64) |
| 6 | 6 | (1:64) | 4 | (1:16) | 9 | (1:512) |
| 7 | 4 | (1:16) | 7 | (1:128) | 4 | (1:16) |
| 8 | 5 | (1:32) | 3 | (1:8) | 8 | (1:256) |
| 9 | 7 | (1:128) | 8 | (1:256) | 8 | (1:256) |
| 10 | 5 | (1:32) | 3 | (1:8) | 8 | (1:256) |

Type 2 sIPV having 8 DU/dose with adjuvant gave equivalent sero conversion as compared to Salk IPV vaccine with 8 DU/dose.

TABLE 6-continued

| Type 3 | | | | | | |
|---|---|---|---|---|---|---|
| | Group 1 | | Group 2 | | Group 3 | |
| | Al(OH)3 Adjuvanted | | | | | |
| | 10 DU 0.6 mgOH | | 5 DU 0.6 mgOH | | 2.5 DU 0.6 mgOH | |
| Rat No | SNT +ve | Sera Titer | SNT +ve | Sera Titer | SNT +ve | Sera Titer |
| 6 | 4 | (1:16) | 1 | (1:2) | 1 | (1:2) |
| 7 | 9 | (1:512) | 0 | (<1:2) | 2 | (1:4) |
| 8 | 7 | (1:128) | 2 | (1:4) | 2 | (1:4) |
| 9 | 1 | (1:2) | 0 | (<1:2) | 1 | (1:2) |
| 10 | 5 | (1:32) | 7 | (1:128 | 1 | (1:2) |

It was found that Type 3 sIPV having 10 DU/dose with adjuvant gave equivalent sero conversion as compared to Salk IPV vaccine with 32 DU/dose.

TABLE 7

| Maximum dose reduction observed for individual Sabin Type 1, 2 & 3 after studies. | | | |
|---|---|---|---|
| sIPV | Standard dose | *SIIL Dose | Dose reduction |
| Type 1 | 40 DU | 5 DU | ~8 Folds |
| Type 2 | 8 DU | 8 DU | Equivalent |
| Type 3 | 32 DU | 10 DU | ~3 Folds |

SIIL: Serum Institute of India In House dose reduced IPV preparation.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I. Immune Response of the Adjuvanted SABIN Polio Viruses.

We observed that if the viruses are adjuvanted with Al $(OH)_3$ shows excellent dose sparing.

If we consider single dose regimen for immunization then 5-16-10 D-Ag are best combination for Sabin's polio type 1, 2 and 3 respectively.

If we consider two doses for immunization then 2.5-8-5 gives excellent immunity.

| | Type 1 | Type 2 | Type 3 |
|---|---|---|---|
| D-Antigen units of Sabin's strain | 5 | 16 | 10 |
| | 2.5 | 8 | 5 |
| | 7.5 | 16 | 10 |

II. Immune Response of the Adjuvanted SALK Polio Viruses.

We observed that if the viruses are adjuvanted with Al $(OH)_3$ shows excellent dose sparing.

If we consider single dose regimen for immunization then 8-2-5 D-Ag are best combination for Salk's polio type 1, 2 and 3 respectively.

If we consider two doses for immunization then 5-2-5 gives excellent immunity.

| | Type 1 | Type 2 | Type 3 |
|---|---|---|---|
| D-antigen units for Salk Strain | 8 | 2 | 5 |
| | 5 | 2 | 5 |

| Rat | 5-16-10 With Alum | | | | | | 2.5-8-5 With Alum | | | | | | 7.5-16-10 With Alum | | | | | |
|---|---|---|---|---|---|---|---|---|---|---|---|---|---|---|---|---|---|---|
| | Single Dose | | | Double Dose | | | Single Dose | | | Double Dose | | | Single Dose | | | Double Dose | | |
| | Type | | | | | | | | | | | | | | | | | |
| No | 1 | 2 | 3 | 1 | 2 | 3 | 1 | 2 | 3 | 1 | 2 | 3 | 1 | 2 | 3 | 1 | 2 | 3 |
| 1 | 8 | 4 | 10 | 12 | 7 | 12 | 5 | 5 | 3 | 7 | 7 | 12 | 8 | 4 | 10 | 9 | 8 | 10 |
| 2 | 6 | 7 | 12 | 11 | 7 | 12 | 5 | 5 | 8 | 5 | 9 | 8 | 9 | 2 | 9 | 12 | 6 | 12 |
| 3 | 6 | 2 | 9 | 6 | 8 | 12 | 5 | 4 | 3 | 8 | 7 | 12 | 11 | 0 | 10 | 8 | 7 | 12 |
| 4 | 6 | 4 | 9 | 7 | 7 | 12 | 6 | 3 | 11 | 9 | 7 | 12 | 7 | 7 | 7 | 7 | 6 | 12 |
| 5 | 8 | 4 | 11 | 9 | 10 | 12 | 10 | 0 | 7 | 10 | 7 | 12 | 11 | 6 | 10 | 9 | 8 | 12 |
| 6 | 6 | 4 | 11 | 10 | 8 | 12 | 6 | 3 | 7 | 9 | 8 | 12 | 6 | 6 | 11 | 9 | 6 | 12 |
| 7 | 6 | 6 | 8 | 11 | 9 | 12 | 5 | 4 | 8 | 8 | 6 | 12 | 6 | 5 | 10 | 11 | 6 | 12 |
| 8 | 6 | 6 | 9 | 9 | 7 | 12 | 7 | 3 | 7 | 10 | 9 | 11 | 6 | 4 | 9 | 9 | 5 | 10 |
| 9 | 7 | 8 | 5 | 10 | 6 | 12 | 5 | 5 | 11 | 10 | 9 | 12 | 7 | 4 | 12 | 10 | 5 | 11 |
| 10 | 5 | 3 | 5 | 11 | 9 | 12 | 7 | 5 | 8 | 10 | 10 | 12 | 10 | 3 | 9 | 9 | 7 | 12 |

| | Positive Control-Tri. Salk IPV | | | | | | Negative Control | | | | | |
|---|---|---|---|---|---|---|---|---|---|---|---|---|
| | Single Dose | | | Double Dose | | | Single Dose | | | Double Dose | | |
| Rat No | Type 1 | Type 2 | Type 3 | Type 1 | Type 2 | Type 3 | Type 1 | Type 2 | Type 3 | Type 1 | Type 2 | Type 3 |
| 1 | 1 | 4 | 2 | 4 | 7 | 9 | 0 | 0 | 0 | 0 | 0 | 0 |
| 2 | 0 | 3 | 0 | 3 | 4 | 8 | 0 | 0 | 0 | 0 | 0 | 0 |
| 3 | 0 | 5 | 4 | 2 | 4 | 9 | 0 | 0 | 0 | 0 | 0 | 0 |
| 4 | 0 | 5 | 3 | 6 | 7 | 7 | 0 | 0 | 0 | 0 | 0 | 0 |
| 5 | NA | NA | NA | NA | NA | NA | 0 | 0 | 0 | 0 | 0 | 0 |
| 6 | 2 | 6 | 5 | 1 | 7 | 6 | 0 | 0 | 0 | 0 | 0 | 0 |
| 7 | 0 | 6 | 2 | 7 | 10 | 9 | 0 | 0 | 0 | 0 | 0 | 0 |
| 8 | 0 | 5 | 1 | 5 | 8 | 8 | 0 | 0 | 0 | 0 | 0 | 0 |
| 9 | 0 | 4 | 2 | 5 | 7 | 9 | 0 | 0 | 0 | 0 | 0 | 0 |
| 10 | 4 | 5 | 4 | 0 | 0 | 0 | 0 | 0 | 0 | 0 | 0 | 0 |

| Salk 8-2-5 With Alum | | | | | | Salk 5-2-5 With Alum | | | | | |
|---|---|---|---|---|---|---|---|---|---|---|---|
| Single Dose | | | Double Dose | | | Single Dose | | | Double Dose | | |
| Type 1 | Type 2 | Type 3 | Type 1 | Type 2 | Type 3 | Type 1 | Type 2 | Type 3 | Type 1 | Type 2 | Type 3 |
| 3 | 8 | 1 | 9 | 10 | 6 | 2 | 8 | 1 | 10 | 11 | 12 |
| 5 | 6 | 2 | 9 | 12 | 8 | 2 | 6 | 2 | 10 | 10 | 10 |
| 4 | 7 | 5 | 12 | 11 | 12 | 4 | 5 | 2 | 9 | 10 | 11 |
| 7 | 5 | 6 | 11 | 11 | 10 | 6 | 7 | 1 | 12 | 12 | 9 |
| 8 | 6 | 3 | 10 | 12 | 11 | 5 | 5 | 5 | 8 | 9 | 6 |
| 5 | 8 | 4 | 10 | 10 | 9 | 2 | 8 | 4 | 11 | 10 | 8 |
| 2 | 7 | 2 | 8 | 9 | 8 | 3 | 6 | 6 | 8 | 12 | 8 |
| 4 | 5 | 1 | 9 | 12 | 7 | 6 | 9 | 2 | 9 | 9 | 9 |
| 5 | 6 | 2 | 8 | 9 | 6 | 2 | 8 | 1 | 10 | 8 | 10 |
| 3 | 9 | 1 | 12 | 10 | 10 | 1 | 7 | 3 | 12 | 12 | 11 |
| Positive Control-Tri. Salk IPV | | | | | | Negative Control | | | | | |
| Single Dose | | | Double Dose | | | Single Dose | | | Double Dose | | |
| Type 1 | Type 2 | Type 3 | Type 1 | Type 2 | Type 3 | Type 1 | Type 2 | Type 3 | Type 1 | Type 2 | Type 3 |
| 2 | 8 | 2 | 2 | 6 | 1 | 0 | 0 | 0 | 0 | 0 | 0 |
| 3 | 10 | 0 | 4 | 5 | 5 | 0 | 0 | 0 | 0 | 0 | 0 |
| 4 | 7 | 3 | 5 | 7 | 8 | 0 | 0 | 0 | 0 | 0 | 0 |
| 0 | 4 | 7 | 5 | 7 | 5 | 0 | 0 | 0 | 0 | 0 | 0 |
| 4 | 5 | 4 | 3 | 9 | 11 | 0 | 0 | 0 | 0 | 0 | 0 |
| 0 | 6 | 3 | 8 | 9 | 7 | 0 | 0 | 0 | 0 | 0 | 0 |
| 2 | 10 | 2 | 7 | 8 | 8 | 0 | 0 | 0 | 0 | 0 | 0 |
| NS | NS | NS | 9 | 10 | 9 | 0 | 0 | 0 | 0 | 0 | 0 |
| 3 | 8 | 4 | 3 | 7 | 6 | 0 | 0 | 0 | 0 | 0 | 0 |
| 1 | 9 | 6 | 3 | 8 | 8 | 0 | 0 | 0 | 0 | 0 | 0 |

1. Supporting Experimental Data for Salk (10-2-5) Single Dose

| Polio Salk vaccine 10-2-5 With Adjuvant | | |
|---|---|---|
| Type 1 | Type 2 | Type 3 |
| 1 | 5 | 7 |
| 3 | 5 | 6 |
| 4 | 9 | 3 |
| 4 | 8 | 2 |
| 3 | 9 | 5 |
| 1 | 7 | 7 |
| 3 | 9 | 7 |
| 3 | 11 | 6 |
| 2 | 9 | 5 |
| 1 | 10 | 6 |

2. Supporting Experimental Data for Salk (10-2-12) Single Dose

| Polio Salk vaccine 10-2-12 With Adjuvant | | |
|---|---|---|
| Type 1 | Type 2 | Type 3 |
| 3 | 6 | 9 |
| 2 | 10 | 9 |
| 4 | 9 | 8 |
| 1 | 9 | 10 |
| 2 | 9 | 11 |
| 2 | 7 | 9 |
| 4 | 9 | 9 |
| 3 | 8 | 11 |
| 1 | 10 | 10 |
| 2 | 6 | 12 |

3. Supporting Experimental Data for Salk (5-8-10) Single Dose

| Polio Salk vaccine 5-8-10 With Adjuvant | | |
|---|---|---|
| Type 1 | Type 2 | Type 3 |
| 1 | 8 | 9 |
| 2 | 10 | 7 |
| 1 | 9 | 8 |
| 0 | 11 | 10 |
| 2 | 9 | 11 |
| 1 | 10 | 8 |
| 0 | 9 | 9 |
| 3 | 11 | 12 |
| 0 | 9 | 10 |
| 1 | 8 | 7 |

4. Supporting Experimental Data for Salk (7.5-16-10) Single Dose

| Polio Salk vaccine 7.5-16-10 With Adjuvant | | |
|---|---|---|
| Type 1 | Type 2 | Type 3 |
| 1 | 11 | 8 |
| 2 | 12 | 9 |
| 1 | 10 | 7 |
| 4 | 11 | 10 |
| 3 | 10 | 8 |
| 0 | 9 | 11 |
| 3 | 9 | 10 |
| 2 | 11 | 12 |
| 0 | 12 | 9 |
| 1 | 10 | 7 |

5.

| Positive Reference control (IPV08-143) | | |
|---|---|---|
| Type 1 | Type 2 | Type 3 |
| 1 | 8 | 4 |
| 2 | 9 | 5 |
| 0 | 2 | 2 |
| 0 | 3 | 0 |
| 1 | 4 | 6 |
| 2 | 4 | 3 |
| 2 | 5 | 2 |
| 3 | 9 | 5 |
| 1 | 6 | 3 |
| 3 | 6 | 5 |

We claim:

1. A method for producing a composition comprising Enteroviral poliovirus particles, wherein the method comprises the steps of:

a) purifying Enteroviral particles in a medium comprising a phosphate buffer;

b) exchanging the phosphate buffer of the purified Enteroviral particles of a) for a TRIS buffer;

c) stabilizing the purified and buffer-exchanged Enteroviral particles of b);

d) inactivating the Enteroviral particles of c) by:

(i) adding formalin to the purified Enteroviral particles and stirring for 7 days;

(ii) filtering the product of step (i);

(iii) adding formalin to the product of step (ii) and stirring for 6 days; and (iv) filtering the product of step (iii); wherein:

the TRIS buffer is present at a concentration of 30-70 mM; aggregation of the Enteroviral particles is prevented or reduced; and D-antigen losses are reduced post inactivation by 8 to 10 fold as compared to inactivation in phosphate buffer; and e) adsorbing the inactivated Enteroviral particles on an aluminum salt adjuvant, whereby the percentage adsorption on the aluminum salt adjuvant is at least 95%.

2. The method according to claim 1, wherein the TRIS buffer has a pH of about 6.8 to 7.2 and at a concentration in the range of 30 mM to 70 mM.

3. The method according to claim 1, wherein the aluminum salt adjuvant of step (e) is aluminum hydroxide, aluminum phosphate, or a mixture of both.

4. The method according to claim 3, wherein the aluminum salt adjuvant is aluminum hydroxide having concentration between 1.5 mg/0.5 ml dose and 2.5 mg/0.5 ml dose at a pH of about 6.5.

5. The method according to claim 4, wherein the total aluminum content in the composition is less than 1.2 mg $Al^{3+}$ per 0.5 mL dose, wherein at least 0.4 mg is $Al^{3+}$ for Type 1, at least 0.2 mg is $Al^{3+}$ for Type 2, at least 0.2 mg is $Al^{3+}$ for Type 3.

6. The method according to claim 1, wherein the composition is a vaccine.

7. The method according to claim 6, wherein the Enteroviral particles comprise polioviruses of the Sabin serotypes 1, 2 and 3.

8. The method according to claim 6, wherein the Enteroviral particles comprises a poliovirus of a Salk serotype IPV type 1 (Mahoney strain), IPV type 2 (MEF-1 strain), and/or IPV type 3 (Saukett strain).

9. The method according to claim 6, wherein the vaccine is a dose reduced Inactivated Polio Vaccine (IPV).

10. The method according to claim 9, wherein the dose reduced Inactivated Polio vaccine comprises:

i) inactivated poliovirus type 1 at a dose less than 15 D-antigen units instead of standard dose of 40 DU; and/or ii) inactivated poliovirus type 2 at a dose less than 18 D-antigen units; and/or iii) inactivated poliovirus type 3 at a dose less than 17 D-antigen units instead of standard dose of 32 DU.

11. The method according to claim 10, wherein the dose reduced inactivated Polio vaccine containing Salk or Sabin polioviruses is prepared by a) purifying poliovirus from a medium;

b) stabilizing the purified poliovirus by adding a M-199 medium containing glycine;

c) inactivating the polio virus using formaldehyde 0.025% at 37° C. for 5 to 13 days in presence of TRIS buffer at a concentration between 30 mM to 60 mM to prevent or reduce aggregation of the poliovirus particles thereby reducing the D-antigen losses post inactivation by 8 to 10 fold as compared to phosphate buffer; and d) adsorbing the inactivated poliovirus on Alum hydroxide adjuvant having a concentration between 2 to 2.5 mg/dose, whereby percentage adsorption on Alum hydroxide is greater than 95% for Type 1, Type 2 and Type 3.

12. The method according to claim 10, wherein the dose reduced inactivated Polio vaccine containing Salk or Sabin poliovirus is prepared by:

a) purifying the poliovirus from a medium containing a poliovirus;

b) stabilizing the purified poliovirus by adding a M-199 medium containing glycine;

c) inactivating the polio virus using formaldehyde 0.025% at 37° C. for 5 to 13 days in presence of TRIS buffer at a concentration between 30 mM to 60 mM to prevent or reduce aggregation of the poliovirus particles thereby reducing the D-antigen losses post inactivation by 8 to 10 fold as compared to phosphate buffer; and d) absorbing the inactivated poliovirus on Alum hydroxide adjuvant having concentration between 2 to 2.5 mg/dose, wherein the percentage adsorption on Alum hydroxide is greater than 95% for Type 1 and Type 3.

13. The method according to claim 10, wherein the dose reduced Inactivated Polio vaccine is:

i) Sabin single dose composition having Sabin Type 1, Type 2, Type 3 combination that is 5-16-10;

ii) Sabin two dose composition having Sabin Type 1, Type 2, Type 3 combination that is 5-16-10;

iii) Sabin single dose composition having Sabin Type 1, Type 2, Type 3 combination that is 2.5-8-5;

iv) Sabin two dose composition having Sabin Type 1, Type 2, Type 3 combination that is 2.5-8-5;

v) Sabin single dose composition having Sabin Type 1, Type 2, Type 3 combination that is 5-8-10;

vi) Sabin two dose composition having Sabin Type 1, Type 2, Type 3 combination that is 5-8-10;

vii) Salk single dose composition having Sabin Type 1, Type 2, Type 3 combination that is 6.5-16-10;

viii) Salk two dose composition having Sabin Type 1, Type 2, Type 3 combination that is 6.5-16-10;

ix) Salk single dose composition having Salk Type 1, Type 2, Type 3 combination that is 8-2-5;

x) Salk two dose composition having Salk Type 1, Type 2, Type 3 combination that is 8-2-5;

xi) Salk single dose composition having Salk Type 1, Type 2, Type 3 combination that is 10-2-5;

xii) Salk two dose composition having Salk Type 1, Type 2, Type 3 combination that is 10-2-5;

xiii) Salk single dose composition having Salk Type 1, Type 2, Type 3 combination that is 10-2-12;

xiv) Salk two dose composition having Salk Type 1, Type 2, Type 3 combination that is 10-2-12;

xv) Salk single dose composition having Salk Type 1, Type 2, Type 3 combination that is 5-2-5;

xvi) Salk two dose composition having Salk Type 1, Type 2, Type 3 combination that is 5-2-5;

xvii) Salk single dose composition having Salk Type 1, Type 2, Type 3 combination that is 10-2-10;

xviii) Salk two dose composition having Salk type 1, Type 2, Type 3 combination that is 10-2-10;

xix) Salk single dose composition having Salk Type 1, Type 2, Type 3 combination that is 10-2-16; or xx) Salk two dose composition having Salk type 1, Type 2, Type 3 combination that is 10-2-16.

14. The method according to claim 13, wherein the dose reduced Salk or Sabin Inactivated Polio Vaccine does not comprise Type 2.

15. The method according to claim 13, wherein the vaccine comprises of one or more antigens from a pathogen that is *Haemophilus influenzae* b, *Neisseria meningitidis* type A, *Neisseria meningitidis* type C, *Neisseria meningitidis* type W, *Neisseria meningitidis* type Y, *Neisseria meningitidis* type X, *Neisseria meningitidis* type B, *Streptococcus pneumoniae, Salmonella typhi*, Hepatitis A, Hepatitis B, diphtheria toxoid, tetanus toxoid, whole cell pertussis, or acellular pertussis.

16. A method for preparing a dose reduced inactivated Polio vaccine containing Salk or Sabin poliovirus, comprising:

a) purifying the poliovirus from a medium comprising a poliovirus and a phosphate buffer;

b) exchanging the phosphate buffer of the purified Enteroviral particles of a) for a TRIS buffer;

c) stabilizing the purified and buffer-exchanged poliovirus of b) by adding a M-199 medium containing glycine;

d) inactivating the poliovirus of c) using formaldehyde 0.025% at 37° C. for 5 to 13 days in presence of TRIS buffer at a concentration between 30 mM to 60 mM to prevent or reduce aggregation of the poliovirus particles thereby reducing the D-antigen losses post inactivation by 8 to 10 fold as compared to phosphate buffer; and e) adsorbing the inactivated poliovirus on an Alum hydroxide adjuvant having concentration between 2 to 2.5 mg/dose, whereby percentage adsorption on Alum hydroxide is greater than 95% for Type 1, Type 2 and Type 3.

17. The method according to claim 3, wherein the TRIS has a 40 mM concentration.

18. The method according to claim 4, wherein the aluminum salt adjuvant has a concentration between 2.100 mg/0.5 ml dose and 2.4 mg/0.5 ml dose at a pH of about 6.5.

19. The method according to claim 5, wherein the total aluminum content in the composition is 0.8 to 1.2 mg $Al^{3+}$ per 0.5 mL dose.

20. A method for producing a composition comprising Enteroviral poliovirus particles, wherein the method comprises the steps of:

a) purifying Enteroviral particles comprising:

(i) concentrating a solution comprising the Enteroviral particles using tangential flow filtration;

(ii) diafiltering the product of step a-i with a medium comprising a phosphate buffer; and (iii) concentrating the product of step a-ii using column chromatography and a phosphate buffer;

b) exchanging the phosphate buffer of the product of step a-iii for a TRIS buffer having a concentration of 30 to 50 mM of TRIS and a pH of 6.8 to 7.2;

c) stabilizing the purified and buffer-exchanged Enteroviral particles by adding a medium comprising glycine to the product of step b;

d) inactivating the Enteroviral particles of c) by:

(i) adding formalin to the purified Enteroviral particles and stirring for 7 days;

(ii) filtering the product of step (i);

(iii) adding formalin to the product of step (ii) and stirring for 6 days; and (iv) filtering the product of step (iii), wherein:

aggregation of the Enteroviral particles is prevented or reduced; and D-antigen losses are reduced post inactivation by 8 to 10 fold as compared to phosphate buffer; and e) adsorbing Enteroviral particles on an Al(OH)3 adjuvant, whereby the percentage adsorption on the adjuvant is at least 95%.

21. The method of claim 20, wherein step a comprises 40 mM of a phosphate buffer at a pH of 7.0 and step c comprises 0.5% glycine.

* * * * *